United States Patent
Allison et al.

(10) Patent No.: US 10,126,180 B2
(45) Date of Patent: Nov. 13, 2018

(54) APPARATUSES FOR NON-INVASIVELY SENSING INTERNAL TEMPERATURE

(71) Applicant: Brain Temp, Inc., Englewood, CO (US)

(72) Inventors: Robert C. Allison, Rancho Palos Verdes, CA (US); Leroy D. Geist, Aurora, CO (US)

(73) Assignee: BRAIN TEMP INC., Bryn Mawr, PA (US)

( * ) Notice: Subject to any disclaimer, the term of this patent is extended or adjusted under 35 U.S.C. 154(b) by 670 days.

(21) Appl. No.: 14/497,312

(22) Filed: Sep. 25, 2014

(65) Prior Publication Data

US 2015/0092817 A1 Apr. 2, 2015

Related U.S. Application Data

(60) Provisional application No. 61/883,980, filed on Sep. 27, 2013.

(51) Int. Cl.
*G01K 11/00* (2006.01)
*A61B 5/00* (2006.01)
(Continued)

(52) U.S. Cl.
CPC ............ *G01K 11/006* (2013.01); *A61B 5/002* (2013.01); *A61B 5/0008* (2013.01); *A61B 5/01* (2013.01);
(Continued)

(58) Field of Classification Search
CPC ... G01K 11/006; A61B 5/0008; A61B 5/0507; A61B 5/01
(Continued)

(56) References Cited

U.S. PATENT DOCUMENTS

| 4,647,281 A * | 3/1987 | Carr ......................... A61B 5/01 |
| | | 343/718 |
| 5,724,030 A * | 3/1998 | Urbas .................. A01K 11/006 |
| | | 340/10.34 |

(Continued)

FOREIGN PATENT DOCUMENTS

| JP | A 2007527736 | 10/2007 |
| WO | 2013/090047 A2 | 6/2013 |

OTHER PUBLICATIONS

European Extended Search Report in EP 14847997.5, dated May 2, 2017, 8 pages.

(Continued)

*Primary Examiner* — Daniel S Larkin
*Assistant Examiner* — Anthony W Megna Fuentes
(74) *Attorney, Agent, or Firm* — Wiggin and Dana LLP; Joseph Casino; Andrew D. Bochner

(57) ABSTRACT

A transducer for noninvasively determining an internal temperature of a location of interest in a body of a subject may be configured to receive native temperature signals originating from the location of interest without substantially receiving interfering signals. Such a transducer may include one or more shielding features for preventing interference. In addition, such a transducer may include a dielectric cavity configured or positioned to increase the native temperature signals sensed, or received, by the antenna. A transducer may be configured to multiplex signals that are indicative of a temperature of a location of interest within the body of a subject and reference temperature signals. Such a transducer may include a connector that facilitates the communication of a multiplexed signal, such as a connector for a coaxial cable. The connector of a transducer may be configured to swivel relative to an end of a cable that (Continued)

has been coupled thereto. Systems including such a transducer are also disclosed.

2 Claims, 5 Drawing Sheets

(51) Int. Cl.
  *A61B 5/05* (2006.01)
  *A61B 5/01* (2006.01)
(52) U.S. Cl.
  CPC .......... *A61B 5/0507* (2013.01); *A61B 5/6833* (2013.01); *A61B 5/4064* (2013.01); *A61B 2560/0412* (2013.01); *A61B 2562/182* (2013.01)
(58) Field of Classification Search
  USPC ................................. 374/120; 600/474, 549
  See application file for complete search history.

(56) References Cited

U.S. PATENT DOCUMENTS

| | | | |
|---|---|---|---|
| 5,829,121 A | 11/1998 | Shoemaker et al. | |
| 6,463,336 B1* | 10/2002 | Mawhinney | A61N 1/40 600/14 |
| 6,511,478 B1* | 1/2003 | Burnside | A61B 18/1492 600/549 |
| 7,124,041 B1 | 10/2006 | Johnson et al. | |
| 7,197,356 B2 | 3/2007 | Carr | |
| 7,484,887 B2 | 2/2009 | Shidemantle et al. | |
| 7,641,390 B2 | 1/2010 | Shidemantle et al. | |
| 8,062,228 B2 | 11/2011 | Carr | |
| 2004/0104852 A1 | 6/2004 | Choi et al. | |
| 2004/0147852 A1* | 7/2004 | Brister | A61B 5/015 600/549 |
| 2005/0043631 A1* | 2/2005 | Fraden | A61B 5/01 600/474 |
| 2006/0060374 A1* | 3/2006 | Trieb | H01R 9/032 174/113 A |
| 2006/0122473 A1 | 6/2006 | Kill et al. | |
| 2006/0155183 A1 | 7/2006 | Kroecker et al. | |
| 2007/0264872 A1* | 11/2007 | Kuroda | H01P 5/085 439/581 |
| 2009/0012417 A1* | 1/2009 | Carr | A61B 5/015 600/549 |
| 2009/0105605 A1 | 4/2009 | Abreu | |
| 2012/0043464 A1 | 2/2012 | Kryskowski et al. | |
| 2012/0057588 A1* | 3/2012 | Duzdar | H01P 1/213 370/339 |
| 2012/0065540 A1* | 3/2012 | Yarden | A61B 5/01 600/549 |
| 2012/0215113 A1* | 8/2012 | Yarden | G01K 1/16 600/474 |
| 2012/0283534 A1 | 11/2012 | Carr et al. | |
| 2013/0072048 A1* | 3/2013 | Schafer | H01R 13/622 439/372 |
| 2013/0130558 A1 | 5/2013 | Ju et al. | |

OTHER PUBLICATIONS

International Search Report in PCT/US2014/057564, dated May 6, 2015, 5 pages.
Written Opinion of the International Search Authority in PCT/US2014/057564, dated May 6, 2015, 5 pages.
International Preliminary Report on Patentability in PCT/US2014/057564, dated Mar. 29, 2016, 6 pages.

* cited by examiner

APPARATUSES FOR NON-INVASIVELY SENSING INTERNAL TEMPERATURE

CROSS-REFERENCE TO RELATED APPLICATION

A claim for the benefit of priority to the Sep. 28, 2013 filing date of U.S. Provisional Patent Application No. 61/883,980, titled APPARATUSES FOR NON-INVASIVELY SENSING INTERNAL TEMPERATURE ("the '980 Provisional Application"), is hereby made pursuant to 35 U.S.C. § 119(e). The entire disclosure of the '980 Provisional Application is hereby incorporated herein.

TECHNICAL FIELD

This disclosure relates generally to apparatuses for determining a temperature of at least a portion of a body of a subject and, more specifically, to apparatuses for noninvasively determining body temperature. More specifically, the disclosed subject matter relates to apparatuses for noninvasively determining a temperature within a body of a subject, such as brain temperature.

SUMMARY

An apparatus according to this disclosure, which is also referred to as a "transducer," noninvasively senses an indicator of a temperature within a body of a subject; i.e., an indicator of an internal temperature, or a "native temperature signal." The transducer may be configured to be positioned against a portion of the body of the subject that is adjacent to or near a location for which a temperature measurement is to be obtained, or a "location of interest" within the subject's body. To enable such noninvasive sensing, the transducer may be configured to be positioned against or adjacent to an exterior surface of the subject's body, or against or adjacent to a portion of the subject's body that is readily accessible from the exterior of the subject's body.

A transducer for noninvasively sensing an indicator of internal temperature may be configured as a low profile apparatus with a sensor that is configured to receive the indicator of internal temperature from the location of interest. A contact side of the transducer is the side of the transducer that is configured to face the location of interest, while an outside of the transducer is configured to face away from the location of interest.

The contact side of the transducer may comprise a receiving aperture, through which an indicator of internal temperature may pass, or be transmitted, to the sensor. The receiving aperture may comprise an opening in the contact side of the transducer or it may comprise a solid material through which the indicator of internal temperature may pass.

The transducer may be configured to receive the indicator of internal temperature from the location of interest without substantial interference. In this regard, the transducer may include one or more shielding features for preventing interference between the indicator of internal temperature and external factors that compete with the indicator, which external factors are also referred to herein as "noise" and as "interference." In a specific, but non-limiting embodiment, the sensor of the transducer may comprise an antenna for receiving microwaves, which are an indicator of temperature within the body of the subject, that originate from the location of interest and the one or more shielding features be configured to prevent microwaves from other sources from reaching the sensor. More specifically, the one or more shielding features may comprise a conductive coating or conductive film. The one or more shielding features may be located on portions of the transducer that will face away from the body of the subject or, even more specifically, away from the location of interest, upon positioning the transducer in a manner that will enable it to sense microwaves that originate from the location of interest. Optionally, one or more shielding features may be located on portions of the contact side of the transducer; for example, around a periphery of the contact side.

The transducer may include a dielectric cavity between the one or more shielding features and a back side of the sensor. The dielectric cavity may prevent electrical shorting between the one or more shielding features and the sensor. Accordingly, the dielectric cavity may be formed from an electrically insulative, or dielectric, material (i.e., a material with a low dielectric constant, K), including solid materials, porous materials and gases. In a specific, but non-limiting embodiment, the dielectric cavity may have a thickness (i.e., the distance between the back side of the sensor and an inner surface of a shielding feature) of about fifty thousandths (0.050) of an inch (e.g., 0.040 inch, 0.060 inch, etc.). The dielectric cavity may function in conjunction with one or more shielding features to prevent noise or interference from reaching the back side of the sensor and, thus, the back side of the antenna.

In some embodiments, a transducer may include a communication element for transmitting internal temperature signals, which are also referred to herein as "intermediate temperature signals," from the sensor to a monitor (e.g., a radiometer in embodiments where the sensor is configured to receive microwaves or other frequencies of electromagnetic radiation, etc.). The communication element may comprise a connector for a cable. In some embodiments, the communication element may be configured to enable one or both of the transducer and an end of the cable to swivel relative to one another, which may accommodate movement by a subject while sensing an indicator of an internal temperature of the subject. In some embodiments, a coaxial cable connector (and a coaxial cable) may enable an end of a cable to swivel relative to the transducer while intermediate temperature signals are being transmitted from the sensor of the transducer to a separate monitor.

The transducer may also include a reference temperature sensor. Such a transducer may be configured to multiplex intermediate temperature signals from the sensor and reference temperature signals from the reference temperature sensor. The multiplexed signals may be conveyed through a communication element, such as a cable connector, of the transducer, to a complementary communication element of a monitor, which may be configured to demultiplex the signals (if they were multiplexed by the transducer) and process signals from the transducer.

Other aspects, as well as features and advantages of various aspects, of the disclosed subject matter will become apparent to those of ordinary skill in the art through consideration of the ensuing description, the accompanying drawings and the appended claims.

DETAILED DESCRIPTION

Figure 1:
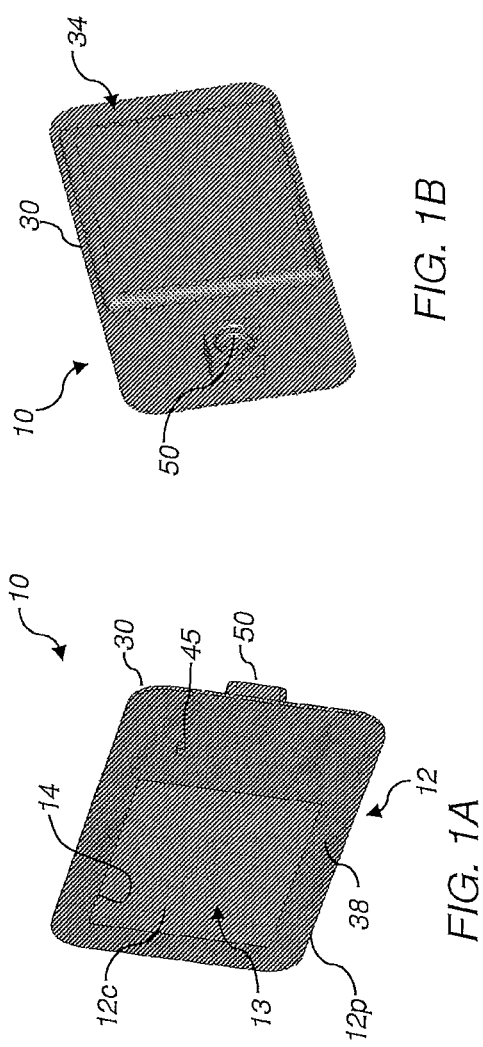
FIGS. 1A and 1B illustrate an embodiment of an apparatus, or transducer, for non-invasively sensing an internal temperature of a portion of a body of a subject.

As shown in FIGS. 1A through 3, a transducer 10 according to this disclosure comprises a low profile apparatus that is configured to noninvasively sense an indicator of an internal temperature within a portion of a body of a subject. Thus, the transducer 10 may include a sensor 20 and a communication element 50 for conveying signals from the sensor 20 to an external monitor 60 (see FIG. 3). In addition, a housing 30 of the transducer 10 may carry the sensor 20.

The transducer 10 includes a contact side 12 and an outside 16. The contact side 12 of the transducer 10 may be configured to face a location of interest L (FIG. 3) within the body B of a subject, while the outside 16 of the transducer 10 may be configured to face away from the location of interest L. At its contact side 12, the transducer 10 may include a receiving aperture 13, through which an indicator of internal temperature, or a native temperature signal $S_N$, may pass, or be transmitted, to the sensor 20. The receiving aperture 13 may comprise an opening in the contact side 12 of the transducer 10 or a solid material (e.g., one or more of a dielectric material, an adhesive material, etc.).

Figure 2:
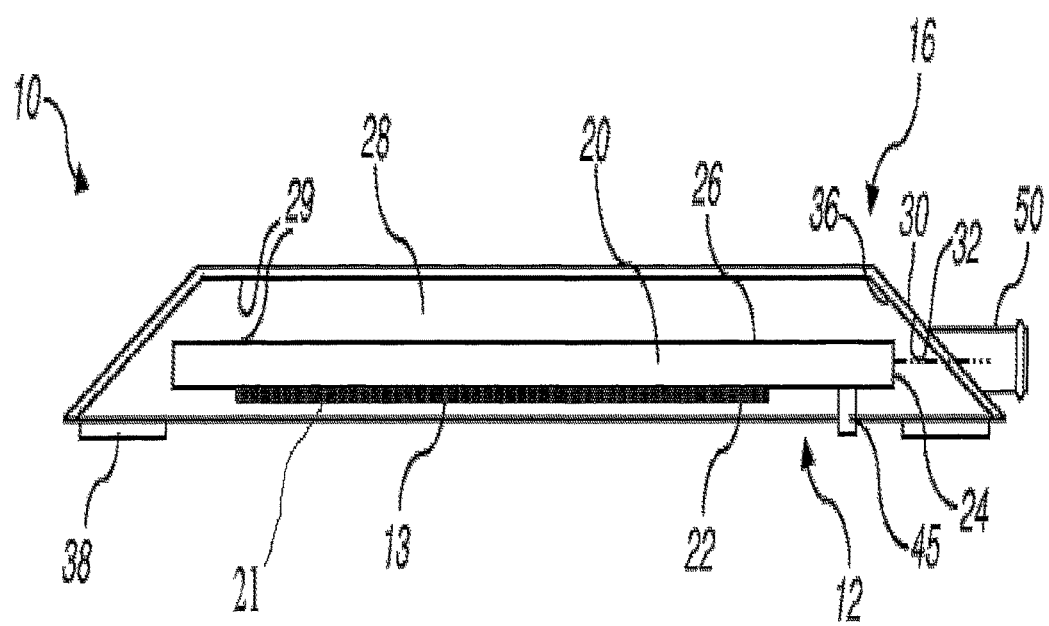
FIG. 2 is a cross-sectional representation of the embodiment of transducer shown in FIGS. 1A and 1B.

The sensor 20, which is depicted by FIG. 2, is configured to receive one or more native temperature signals SN from the location of interest L within the body B of the subject. In some embodiments, the sensor 20 may include one or more antennas 21 from receiving native temperature signals SN that comprise electromagnetic radiation in the so-called "microwave" portion of the electromagnetic spectrum. Without limitation, in a specific embodiment, the range of frequencies of microwave radiation that may be received by the sensor 20 may include native temperature signals SN having frequencies in the range of about 4 GHz±200 MHz. Specific embodiments of such a sensor 20, which comprise electrically conductive features of a printed circuit board (PCB), are disclosed by PCT International Publication No. WO 2013/090047 A2 of Meridian Medical Systems, LLC, which was published on Jun. 20, 2013, the entire disclosure of which is hereby incorporated herein. Such a sensor 20 may receive, and sense, signals that impinge either side-a front side 22 or a back side 26—thereof.

The front side 22 of the sensor 20 faces the contact side 12 of the transducer 10 and, thus, is located adjacent to the receiving aperture 13. The back side 26 of the sensor 20 faces the opposite direction, toward the outside 16 of the transducer 10. When the transducer 10 is positioned on the body B of a subject, the front side 22 of the sensor 20 faces the location of interest L, while its back side 26 faces away from the location of interest L.

In some embodiments, a dielectric cavity 28 may be located over, or even directly adjacent to, the back side 26 of the sensor 20. The dielectric cavity 28 may provide electrical insulation over the back side 26. Without limitation, the dielectric cavity 28 may comprise a dielectric material, which, in some embodiments, may comprise a foam or otherwise include voids (e.g., microspheres, microcapsules, etc.; an open-celled material; a close-celled material; etc.). Alternatively, the dielectric cavity 28 may comprise a void over the back side 26. Such a void may include a gas (e.g., an inert gas, such as argon; nitrogen; etc.), a mixture of gases (e.g., air, etc.) or a vacuum.

One or more shielding features 36 of the transducer 10 may be located over the back side 26 of the sensor 20 to prevent interfering signals $S_X$ (e.g., microwaves, etc.) from sources other than the location of interest L from reaching the back side 26 of the sensor 20 and, thus, from interfering with (e.g., appearing to the sensor 20 to be) native temperature signals $S_N$ from the location of interest L. In embodiments where the transducer 10 includes a dielectric cavity 28, the shielding feature(s) 36 may be positioned over the dielectric cavity 28 or, in embodiments where the dielectric cavity 28 comprises a void, even define a boundary of the dielectric cavity 28.

In various embodiments, the shielding feature(s) 36 may comprise a low resistance electrically conductive material, such as a metal. Such a shielding feature 36 may comprise a film (e.g., plating, a deposited film, etc.), a foil or another structure or group of structures. In some embodiments, shielding features 36 may also be positioned and/or configured to prevent the interfering signals $S_X$ from reaching the front side 22 of the sensor 20.

Figure 3:
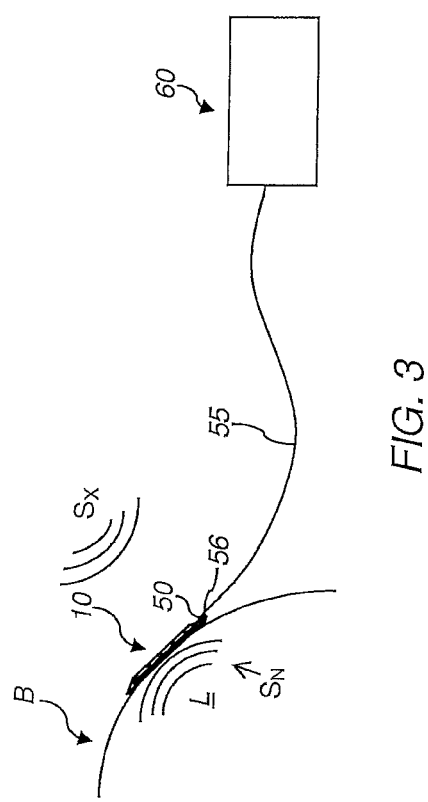
FIG. 3 depicts an embodiment of use of a transducer according to this disclosure.

The receiving aperture 13, the sensor 20, the dielectric cavity 28 (if any) and the shielding features 36 may be defined by and/or carried by a housing 30 of the transducer 10. With continued reference to FIG. 2, the transducer 10 may include a housing 30 that carries the sensor 20 and orients and positions the sensor 20 in a manner that will enable the sensor 20 to receive, or sense, native temperature signals $S_N$ originating from a location of interest L within the body B of a subject (FIG. 3).

In the illustrated embodiment, the housing 30 comprises a rigid structure (e.g., a structure that is molded, pressed, machined, etc.). Alternatively, the housing 30 may comprise a conformal coating (e.g., a film, such as a shrink-wrap film, a deposited polymeric coating, etc.). The housing 30 may define the outside 16 of the transducer 10, toward which the back side 26 of the sensor 20 is oriented. The housing 30 may carry the sensor 20 in a manner that orients the front side 22 of the sensor 20 toward the receiving aperture 13 and the contact side 12 of the transducer 10. In embodiments where a dielectric cavity 28 is located adjacent to, or over, the back side 26 of the sensor 20 and between the back side 26 of the sensor 20 and the outside 16 of the transducer 10, the housing 30 and the back side 26 of the sensor 20 may define the boundaries 29 of the dielectric cavity 28. In some embodiments, a housing 30 may also define at least a portion of the contact side 12 of the transducer 10. As an example, the housing 30 may define at least a portion of the receiving aperture 13.

The housing 30 also carries one or more shielding features 36 of the transducer 10. In the illustrated embodiment, the shielding feature(s) 36 cover(s) the back side 26 of the sensor 20, as well as a periphery 24 of the sensor 20 and a periphery 14 of the receiving aperture 13. As illustrated, the shielding feature(s) 36 may be carried by an interior surface 32 of the housing 30. As an alternative, or in addition, to carrying one or more shielding features 36 on its interior surface 32, the housing 30 may carry one or more shielding features 36 on its exterior surface 34.

The transducer 10 may also include an adhesive material 38 on at least portions of its contact side 12. The adhesive material 38 may be located adjacent to a periphery 12p of the contact side 12 of the transducer 10 and surround a more centrally located portion 12c of the contact side 12. Alternatively, the adhesive material 38 may comprise or substantially cover the contact side 12 of the transducer 10. In such an embodiment, the adhesive material 38 may form a part of or all of the receiving aperture 13 of the transducer 10. In any event, the adhesive material 38 may prevent interfering signals $S_X$ from passing between the contact side 12 of the transducer 10 and a surface against which the contact side 12 is positioned and into the receiving aperture 13 of the transducer 10. The adhesive material 38 may be configured to secure the transducer 10 in place on or over the body of a subject.

Figure 5:
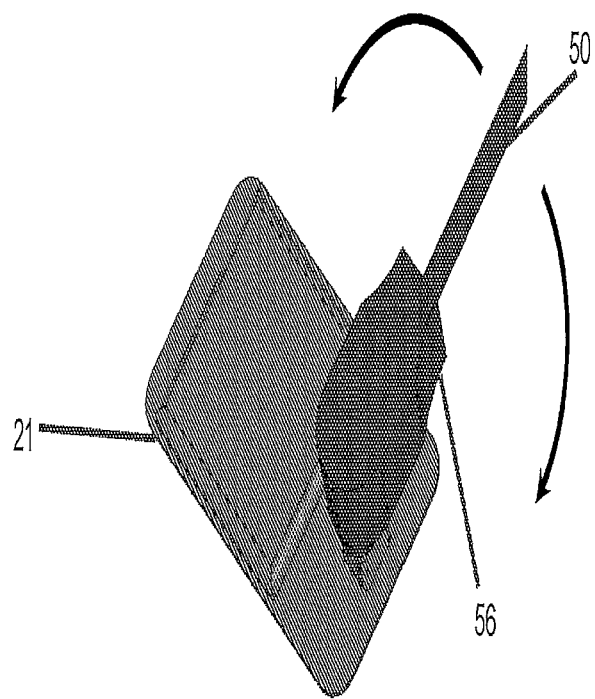
FIG. 5 illustrates an exemplary swivel connector, in accordance with an embodiment.

When a sensor 20 of a transducer 10 senses, or receives, native temperature signals $S_N$, those signals may be converted to electrical signals, which are referred to herein as "intermediate temperature signals." The transducer 10 may be configured to transmit the intermediate temperature signals to a separate, external monitor 60. Accordingly, the transducer 10 may include a communication element 50, which is in communication with the sensor 20 and is configured to communicate with a corresponding element of the external monitor 60. The communication element 50 may be configured to couple with an end 56 of a cable 55 in a manner that enables the one or both of the end 56 and the communication element 50 to swivel relative to the other of the communication element 50 and the end 56 of the cable 55. In an exemplary embodiment, the end 56 an communication element 50 may swivel relative to one another via swivel connector 57, depicted in FIG. 5. In some embodiments, the communication element 50 and the end 56 of the cable 50 may comprise coaxial connectors, as depicted by FIGS. 1A through 3.

In some embodiments, the transducer 10 may also include a reference temperature sensor 45. The reference temperature sensor 45 may be configured to obtain a measurement of a reference temperature, such as a temperature of skin at or adjacent to a location where the transducer 10 is positioned on the body B of a subject. In a specific, but non-limiting embodiment, the reference temperature sensor 45 may comprise a thermistor, a resistance temperature detector (RTD), a thermocouple, an infrared (IR) temperature sensor or the like.

Figure 4:
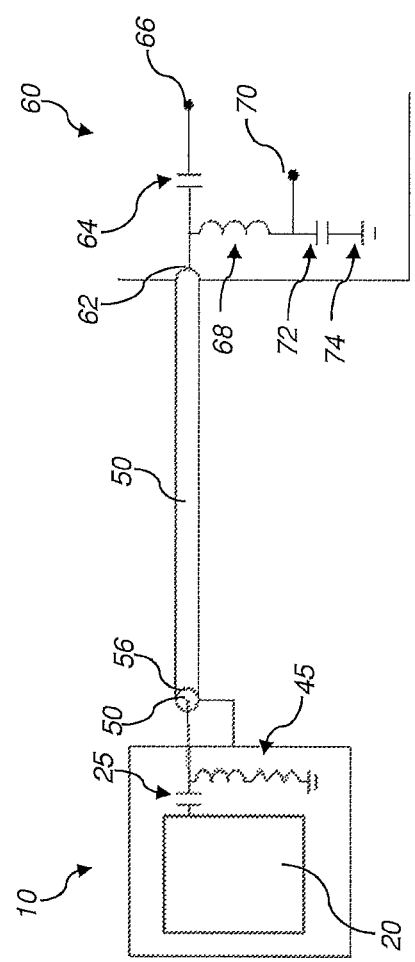
FIG. 4 is a schematic representation of an embodiment of an electrical circuit of an embodiment of transducer according to this disclosure.

The transducer 10 may include one or more components (e.g., circuitry, etc.), which may be carried by the sensor 20 (e.g., by a circuit board that defines the sensor, etc.), configured to multiplex intermediate temperature signals and reference temperature signals from the reference temperature sensor 45. Turning now to FIG. 4, a schematic representation of an embodiment of an electrical circuit that enables such multiplexing is depicted. Specifically, FIG. 4 illustrates the sensor 20, a capacitor 25 including a conductor in communication with sensor 20, a reference temperature sensor 45 in communication with an opposite conductor of the capacitor 25, and a communication element 50 (e.g., a cable connector, etc.) in series with the reference temperature sensor 45. This arrangement may enable multiplexing of the intermediate temperature signal from the sensor 20 and the reference temperature signal from the reference temperature sensor 45.

With continued reference to FIG. 4, the communication element 50 of a transducer 10 may be configured to enable intermediate temperature signals from the sensor 20 to be communicated to a monitor 60, as disclosed previously. Optionally, in embodiments where a transducer 10 includes a reference temperature sensor 45, the communication element 50 may also enable the communication of reference temperature signals to the monitor 60.

The monitor 60 may include a communication element 62 for receiving signals from the communication element 50 of the transducer 10. Accordingly, the communication element 62 of the monitor 60 may be configured in a manner that complements a configuration of the communication element 50 of the transducer 10. In a non-limiting example, where the communication element 50 comprises a coaxial cable connector and the cable 55 comprises a coaxial cable, the communication element 62 of the monitor 60 may also comprise a coaxial cable connector.

Signals that are received by the communication element 62 of the monitor 60 are conducted to a first capacitor 64 and to an inductor 68, which are in parallel with one another. Signals that cross the first capacitor 64 are conducted to one or more radiometers 66, which convert each received signal to a voltage. Signals that pass through the inductor 68 are conducted to a thermistor output 70 or to a second capacitor 72, which are in parallel with one another. The second capacitor 72 is connected to a ground 74. This arrangement enables demultiplexing of the intermediate temperature signals from the reference temperature signals and, optionally, one or more other signals. More specifically, the first capacitor 64 ensures that only the intermediate temperature signal is conveyed to the radiometer(s) 66, while the second capacitor 72 and ground 74 ensure that only the reference temperature signal is conveyed to the thermistor output 70.

The monitor 60 may be configured to process the signals in a manner that provides a desired output.

Although the foregoing description sets forth many specifics, these should not be construed as limiting the scope of any of the claims, but merely as providing illustrations of some embodiments and variations of elements or features of the disclosed subject matter. Other embodiments of the disclosed subject matter may be devised which do not depart from the spirit or scope of any of the claims. Features from different embodiments may be employed in combination. Accordingly, the scope of each claim is limited only by its plain language and the legal equivalents thereto.

What is claimed:

1. A transducer for noninvasively measuring temperature within a body of a subject, comprising: a circuit board including a front side and a back side opposite from the front side, the circuit board defining an antenna for receiving at least one native temperature signal from a location of interest within a body of a subject; wherein the circuit board carries at least a portion of an electrical circuit including the antenna, a capacitor and the thermistor, the capacitor being positioned in series between a receiving aperture and the thermistor, the thermistor being in direct communication with the cable connector; a reference temperature sensor; and a coaxial cable connector for transmitting a multiplexed signal including an intermediate temperature signal from the antenna and a reference temperature signal from the reference temperature sensor, wherein the coaxial cable connector and an end of a cable are configured to swivel relative to one another upon connecting the end of the cable to the cable connector.

2. The transducer of claim 1, wherein the reference temperature sensor comprises a thermistor.

* * * * *